(12) United States Patent
Bhaskaran et al.

(10) Patent No.: US 9,669,043 B2
(45) Date of Patent: Jun. 6, 2017

(54) SYNERGISTIC PHARMACEUTICAL COMPOSITION FOR SEROTONIN REUPTAKE INHIBITION AND PROCESS OF PREPARATION THEREOF

(75) Inventors: Sunil Bhaskaran, Pune (IN); Mohan Vishwaraman, Pune (IN)

(73) Assignee: INDUS BIOTECH PRIVATE LIMITED, Pune (IN)

(*) Notice: Subject to any disclaimer, the term of this patent is extended or adjusted under 35 U.S.C. 154(b) by 513 days.

(21) Appl. No.: 12/069,766

(22) Filed: Feb. 12, 2008

(65) Prior Publication Data

US 2008/0194499 A1    Aug. 14, 2008

Related U.S. Application Data

(60) Provisional application No. 60/904,034, filed on Feb. 28, 2007.

(30) Foreign Application Priority Data

Feb. 12, 2007 (IN) .......................... 255/MUM/2007

(51) Int. Cl.
| | |
|---|---|
| A61K 31/704 | (2006.01) |
| A61K 31/70 | (2006.01) |
| A61K 31/702 | (2006.01) |
| A61K 36/23 | (2006.01) |

(52) U.S. Cl.
CPC ............ *A61K 31/702* (2013.01); *A61K 36/23* (2013.01)

(58) Field of Classification Search
CPC .............................. A61K 36/23; A61K 31/702
USPC ......... 514/33, 25, 26; 536/4.1, 128; 424/764
See application file for complete search history.

(56) References Cited

U.S. PATENT DOCUMENTS 7,402,669 B2 * 7/2008 Loiseau et al. ............... 536/128

FOREIGN PATENT DOCUMENTS

| CN | 1582952 A | * | 2/2005 |
| EP | 867447 A1 | * | 9/1998 |

OTHER PUBLICATIONS

Cui , CN 1582952 A; Feb. 23, 2005 (Machine, English translation).*
STN abstract of Cui , CN 1582952 A; Feb. 23, 2005 (Abstract sent).*
Complete English-language translation of Chinese Patent Application Publication No. 1582952A dated Feb. 23, 2005.

* cited by examiner

*Primary Examiner* — Shaojia Anna Jiang
*Assistant Examiner* — Michael C Henry
(74) *Attorney, Agent, or Firm* — Oliff PLC

(57) ABSTRACT

The present invention relates to a novel pharmaceutical composition for serotonin reuptake inhibition, wherein the composition comprises pentacyclic terpenoid glycosides, preferably asiaticoside and madecassoside optionally along with excipients. Also the present invention relates to a process of preparation of novel pharmaceutical composition for serotonin reuptake inhibition, wherein the process comprising steps of: (a) obtaining extract from the plant *Centella asiatica*; (b) treating the extract with the solvents to remove fatty substances, chlorophyll and other colorants; (c) purifying the extract through HPLC to obtain the eluted solvent; and (d) concentrating the eluted solvent to arrive at the composition. The invention also relates to the use of a composition comprising pentacyclic terpenoid glycosides, preferably asiaticoside and madecassoside optionally along with excipients to manufacture a medicament for serotonin reuptake inhibition in a subject in need thereof.

23 Claims, 3 Drawing Sheets
(3 of 3 Drawing Sheet(s) Filed in Color)

SYNERGISTIC PHARMACEUTICAL COMPOSITION FOR SEROTONIN REUPTAKE INHIBITION AND PROCESS OF PREPARATION THEREOF

CROSS-REFERENCES TO RELATED APPLICATIONS

This application is entitled to priority pursuant to 35 U.S.C. §119(e) to U.S. provisional patent application 60/904,034, which was filed on 28 Feb. 2007, and is also entitled to priority pursuant to 35 U.S.C. §119(a) to India patent application 00255/MUM/2007, which was filed on 12 Feb. 2007.

BACKGROUND OF THE INVENTION

The invention relates generally to the field of serotonin reuptake inhibitors and their uses.

Serotonin is a neurotransmitter and plays a significant role in many physiological functions. Serotonin is involved in the sensation of satiety which is linked to food intake. This function of Serotonin can be utilized in the treatment of eating disorders and the related management of obesity. Serotonin is also involved in mood elevation and renders a sense of well being. This physiological property can be utilized in applications where this can be offered as a sensory ingredient to elevate mood and sense of well being. The most significant application of Serotonin is in the treatment of the physiological disorder, Depression. This neurotransmitter offers a substantial advantage for the management of a disease like depression. Apart from this Serotonin also plays a role in gastric emptying.

As per NIMH (National Institute of Mental Health) USA, about 18.8 million American Adults, which constitutes 9.5% of the population, suffer from the depression illness. The economic cost of this disorder is very high. However the cost of Human suffering cannot be estimated. A depressive disorder is an illness that affects the body, mood and thoughts. There are different types of depression like major depression, Dysthymia which is a less severe type of depression and bipolar Disorder which is characterized by cycling mood, characterized by several highs (mania) and lows (depression).

The usual symptoms of depression are persistent sadness, anxiousness or empty moods, feelings of hopelessness, feelings of guilt, worthlessness, decreased energy, difficulty in concentrating, Insomnia, overeating, weight gain, thoughts of death, restlessness and irritability. The major cause of depression is the reduction in functional brain monoamines in the amine dependant synaptic transmission. This involves brain monoamines like Norepinphrine (NE), Serotonin (5 HT) and Dopamine.

The Current Methods of Treatment Are:

Tricyclic Anti-Depressants

These drugs raise the amount of the neurotransmitter at the receptor by preventing their uptake into the nerve endings. This leaves more amount of the amine outside the nerve cells which are now able to interact with the receptors. Tricyclic drugs mainly affect the cells which secrete norepinephrine.

Many tricyclics can block receptors for Acetylcholine producing dry mouth, blurred vision and constipation. Some tricyclics can have sedative effects, drowsiness, and increase the risk of low blood pressure.

Selective Serotonin Reuptake Inhibitors (SSRIs)

This group of drugs affects the cells which release 5 Hydroxytryptamine, also called Serotonin. These drugs compensate for a lower than normal amount of Serotonin in some areas of the brain which make them effective in the treatment of depression. The side effects caused by these drugs include headache, insomnia, diarrhea weight loss, and a decrease in sexual function.

Monoamine Oxidase Inhibitors

The second group of drug therapy is Monoamine oxidase inhibitors. Monoamine oxidase is an enzyme which degrades neurotransmitters. The use of these enzyme inhibitor drugs leads to less destruction of amines in nerve endings, thus leaving more available for storage and release by nerve cells. The side effects caused by these drugs include reduction in blood pressure, dry mouth, blurred vision and constipation. These drugs cause very serious reactions with cheese and beer, which leads to significant increase in blood pressure and can cause bleeding in Brain.

It is apparent that the depression is gaining significance and the current methods of treatment for the management of this disease are far from satisfactory. This disorder is chronic in nature and calls for long term management therapy. Therefore it is imperative to develop kinder and gentler methods of treatment derived from botanical sources for the long-term management of this disorder. The present invention is aimed at achieving this goal.

BRIEF SUMMARY OF THE INVENTION

Accordingly the present invention is in relation to a composition for serotonin reuptake inhibition, said composition comprising pentacyclic terpenoid glycosides, preferably asiaticoside and madecassoside optionally along with acceptable excipients; a process for preparation of a composition comprising pentacyclic terpenoid glycosides, preferably asiaticoside and madecassoside, wherein said process comprises steps of: obtaining extract from the plant *Centella asiatica*, filtering and concentrating the extract, dissolving concentrated extract in a solvent to obtain a solution, treating the solution with the solvents to remove fatty substances, chlorophyll and other colorants, passing treated solution through adsorbents to get a clear solution; and concentrating the clear solution to obtain the composition, and a method of treating serotonin mediated disorders in a subject in need thereof, said method comprising step of administering pharmaceutically acceptable amount of composition to the subject.

BRIEF SUMMARY OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
FIG. 1 is an image that represents the stomach of the animal treated with a test drug dose of 30 mg/kg.

This invention relates to a novel pharmaceutical composition for serotonin reuptake inhibition, the composition comprising pentacyclic terpenoid glycosides, along with excipients. This invention is related to a method of preparing a novel pharmaceutical composition for serotonin reuptake inhibition from natural sources. This invention is related to the use of a novel pharmaceutical composition for selective serotonin reuptake inhibition. This invention also relates to the application of this botanical composition in management of Depression, as a sensory compound for mood elevation and other such applications where Serotonin mediated action is involved.

The object of the present invention is a pharmaceutical composition for serotonin reuptake inhibition comprising pentacyclic terpenoid glycosides, preferably asiaticoside and madecassoside optionally along with excipients.

Still another object of the present invention is to develop a process of preparation of novel pharmaceutical composition for serotonin reuptake inhibition.

Yet another object of the present invention is to obtain a novel pharmaceutical composition for serotonin reuptake inhibition useful in the management of depression and serotonin mediated functions.

Still another object of the present invention is to use the composition to manufacture a medicament for serotonin reuptake inhibition in a subject in need thereof.

Still another object of the present invention is to use the composition in treating serotonin mediated disorders, depression, obesity, gastric emptying, mood elevation and other disorders involving serotonin in a subject in need thereof.

DETAILED DESCRIPTION

The present invention relates to a composition for serotonin reuptake inhibition, said composition comprising pentacyclic terpenoid glycosides, preferably asiaticoside and madecassoside optionally along with acceptable excipients.

In another embodiment of the present invention, pentacyclic terpenoid glycosides are obtained from plant or animal sources, preferably from the plant *Centella asiatica*.

In yet another embodiment of the present invention, the concentration of asiaticoside is ranging from 15-50% and concentration of madecassoside is ranging from 20-50%.

In still another embodiment of the present invention, the excipients are selected from a group comprising granulating agents, binding agents, lubricating agents, disintegrating agents, sweetening agents, glidants, anti-adherents, antistatic agents, surfactants, anti-oxidants, gums, coating agents, coloring agents, flavouring agents, coating agents, plasticizers, preservatives, suspending agents, emulsifying agents and spheronization agents.

In still another embodiment of the present invention, said composition is formulated into various dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups, elixirs, phytoceuticals, nutraceuticals and food stuffs.

The present invention is also in relation to a process for preparation of a composition comprising pentacyclic terpenoid glycosides, preferably asiaticoside and madecassoside, wherein said process comprising steps of:
 a. obtaining extract from the plant *Centella asiatica*;
 b. filtering and concentrating the extract;
 c. dissolving concentrated extract in a solvent to obtain a solution;
 d. treating the solution with the solvents to remove fatty substances, chlorophyll and other colorants;
 e. passing treated solution through adsorbents to get a clear solution; and
 f. concentrating the clear solution to obtain the composition.

In still another embodiment of the present invention, the solvent is selected from a group comprising heterocyclic aromatic compounds, aliphatic compounds, ketones, alcohols, nitrites, esters, ether and mixtures of one or more thereof.

In still another embodiment of the present invention, the solvent used for extraction is preferably an aliphatic alcohol.

In still another embodiment of the present invention, the extraction is carried out at temperature ranging from 20° C. to 38° C. preferably at 30° C.

In still another embodiment of the present invention, the extraction is carried out for 6 h to 10 h preferably for 8 h.

In still another embodiment of the present invention, the concentration is carried out at temperature ranging from 40° C. to 50° C. preferably at 45° C.

In still another embodiment of the present invention, the solvent is preferably deionized water.

In still another embodiment of the present invention, the solvent is selected from a group comprising hexane, petroleum ether and methylisobutylketone.

In still another embodiment of the present invention, the adsorbent is selected from a group comprising resin, charcoal, silica gel and a mixture thereof.

In still another embodiment of the present invention, the concentration is carried out at temperature ranging from 50° C. to 65° C.

The present invention is also in relation to a method of treating serotonin mediated disorders in a subject in need thereof, said method comprising step of administering pharmaceutically acceptable amount of composition comprising pentacyclic terpenoid glycosides, preferably asiaticoside and madecassoside optionally along with excipients, to the subject.

In still another embodiment of the present invention, the subject is an animal or human being.

In still another embodiment of the present invention, the composition is administered at a dosage ranging from 15-150 mg/kg body weight in animals and 1-15 mg/kg body weight in human beings.

In still another embodiment of the present invention, the serotonin mediated disorders are depression, obesity, gastric emptying, mood elevation and other disorders involving serotonin.

In still another embodiment of the present invention, the composition is non toxic and free of adverse effects.

One embodiment of the invention relates to a novel pharmaceutical composition for serotonin reuptake inhibition, wherein the composition comprises pentacyclic terpenoid glycosides, preferably asiaticoside and madecassoside, optionally with excipients. In one aspect of the present embodiment the concentration of pentacyclic terpenoid glycosides usually range within asiaticoside 15-50% and madecassoside 20-50%.

In another aspect of the present embodiment, the novel composition is useful in the management of depression and serotonin mediated functions.

Still another embodiment of the present invention is the use of a composition comprising pentacyclic terpenoid glycosides optionally with excipients for the management of depression and serotonin mediated functions in a subject in need thereof. In one aspect of the present embodiment the subject is an animal including human beings.

Depression is a disease that requires sustained medication for its management. The current available methods of treatment take about 2-4 weeks before they have any effect. Due to this requirement of sustained treatment, the subjects experience a range of side effects which vary in severity and duration. The present invention relates to a composition, a process and the use of a composition for the management of depression and other serotonin mediated functions. The present invention is involved in the management of depression and other serotonin mediated functions while producing minimal side effects. As seen in the test described below, the test drug showed lesser agitation, and diarrhea in comparison with a standard SSRI drug. Also the present invention does not produce sedation in the subject.

The present invention also relates to use of a composition comprising pentacyclic terpenoid glycosides, preferably asiaticoside and madecassoside optionally along with excipients to manufacture a medicament for serotonin reuptake inhibition in a subject in need thereof. In still another embodiment of the present invention, serotonin reuptake inhibition is useful in the management of depression and serotonin mediated functions. In still another embodiment of the present invention, the subjects are animals, including human beings.

In still another embodiment of the present invention, composition is either a powder or liquid and has minimal side effects, wherein the composition is in a dosage range of 15-150 mg/kg in animals and 1-15 mg/kg in human beings.

In still another embodiment of the present invention, the whole terrestrial portion of the plant Centella asiatica including the stem and leaves is washed in stream of running water to remove all adhering soil and contaminants and dried under shade. The dried material is pulverized in a hammer mill having an out-put particle size of material able to pass through a 16 mesh size. The pulverized material is packed in a vertical percolater having filter ends in both top and bottom. The solvent used can be an alcohol, including but not limited to methyl alcohol, ethyl alcohol, propyl alcohol, isopropyl alcohol either as single solvent or in a particular combination preferably ethyl alcohol alone or in combination with isopropyl alcohol in a counter current manner at temperatures ranging between 20° C. to 38° C., preferably at 30° C. for a time period ranging between 8 hrs to 24 hrs preferably for 8 hrs.

The resultant extract is filtered clear of any visible particles through an 80 mesh filter and concentrated at low temperature using vacuum concentration facility at or around 40° C. to 50° C. preferably at 45° C. to a paste. The resultant paste is dissolved in deionised water to get uniform solution. This solution is extracted with petroleum ether solvent or hexane to remove all fatty substances. The de-fatted extract is again extracted with methyl isobutylketone to remove chlorophyll and other colorants with Multiple times volume (preferably 4 times) to that of the aqueous extract are used here. The clear aqueous extract is then passed through a bed of adsorbent grade resin and washed free of all the colors and contaminants out of the bed with 5 to 15 volumes or more preferably 8 volumes of deionised water. The water washed bed was eluted with an alcoholic solvent having carbon atom ranging from C-1 to C-4, preferably ethanol and isopropyl alcohol or a mixture of the mentioned alcohols.

The eluted solvent was again cleaned on a bed comprising of a layer of activated charcoal and silica gel having 60-120 mesh particle size. The eluted solvent was collected and the bed repeatedly washed to get all the pentacyclic terpenoid glycosides out of the bed. The solvent elute was concentrated under vacuum at low temperature preferably between 50° C. to 65° C. to a Powder and the resultant powder is suspended in an equal quantity of demineralised water and spray dried to get a Highly water soluble powder having a composition of pentacyclic terpenoid glycosides mainly asiaticoside ranging between 15 to 50% and Madecassoside varying between 20 to 50% in composition by HPLC A summary of the above describes extraction process is as follows:

1. The plant of Centella asiatica is washed with running water to remove all adhering soil and contaminants and dried under shade.

2. The dried material is pulverized in a hammer mill having an output particle size of material passing through 16 mesh size.

3. The pulverized material is packed in a vertical percolator and extracted with an aliphatic alcohol at temperature ranging from 20 to 38° C. preferably for 8 hrs in a countercurrent manner.

4. The resultant extract is filtered clear of any visible particles through a 80 mesh filter and concentrated at low temperature using vacuum concentration facility at or around 40° C. to 50° C. preferably at 45° C. to a paste.

5. The resultant paste is dissolved in deionised water to get a uniform solution.

6. This solution is extracted with petroleum ether solvent or hexane to remove all fatty substances.

7. The above liquid is again extracted with methylisobutylketone to remove chlorophyll and other colorants with multiple times, with a volume preferably 4 times to that of the aqueous extract.

8. The clear aqueous extract is then passed through a bed of adsorbent grade resin.

9. The bed is washed free of all the colors and contaminants out of the bed with 5 volumes or more preferably 8 volumes of deionised water.

10. The water washed bed was eluted with an alcoholic solvent having carbon atom ranging from C-1 to C-4, preferably ethanol and isopropyl alcohol or a mixture of the said alcohols.

11. The eluted solvent was again cleaned up on a bed comprising of a layer of activated charcoal and silica gel having 60-120 mesh particle size.

12. The eluted solvent was collected and the bed repeatedly washed to get all the pentacyclic terpenoid glycosides out of the bed.

13. The solvent elute was concentrated under vacuum at low temperature preferably between 50° C. to 65° C. to a powder.

14. Resultant powder is suspended in equal quantity of demineralised water and spray dried to get a highly water soluble powder having a composition of pentacyclic terpenoid glycosides mainly asiaticoside ranging between 15 to 50% and Madecassoside varying between 20 to 50% in composition by the following HPLC.

HPLC Method:

| Column: 250 mm × 4.6 mm Reversphase C-18 particle size 5µ Wavelength of detector: 220 nm Flowrate: 1.4 ml/min Standard Used: Chromadex | | |
|---|---|---|
| Time | Acetonitrile | Water |
| Initial | 75% | 25% |
| 30 mins | 45% | 55% |
| 40 mins | 75% | 25% |

The resultant purified test compound is subjected to the following tests to ascertain its anti-depressants activity and to establish its mode of action.

In the Tail Suspension Test, the test compound showed significant anti-depressant activity which was measured as a percentage decrease in the immobility of suspended mice. At an oral feed dosage of 30 mg/kg, the test compound showed a 40.3% decrease in immobility. This shows a promising ability of this compound as an anti-depressant.

Another proof of the anti-depressant activity of the drug was seen during the decrease in immobility in the Forced Swim Test. The test drug returned a 68.76% reduction in immobility at 30 mg/kg oral dose compared to 71.44% decrease of standard drug tricyclic anti-depressant drug dosed at 100 mg/kg.

In the Locomotor Activity Test the test compound showed no sedative effects on the mice. This is evidenced by the increase in locomotor activity of the mice. The anti-depressant activity of this drug is not accompanied by sedation and drowsiness.

The test compound demonstrated its serotonin reuptake inhibition ability during the 5-Hydroxytrptophan (5-HTP) Potentiation test, wherein it significantly increased the number of head twitches observed in mice. The test compound at a dose of 100 mg/kg was comparable with a standard SSRI, namely Fluoxetine at a dose of 100 mg/kg. Apart from this the test drug, also showed minimized side effects in comparison with a standard SSRI drug.

Thus the test compound does not have the usual side effect of MAO (Monoamine oxidase) inhibiting activity. Thus this is free of anticholinergic side effect. It has significant dose dependant anti-depressant activity in a tail suspension test in mice.

EXAMPLES

The invention is now described with reference to the following Examples. These Examples are provided for the purpose of illustration only, and the invention is not limited to these Examples, but rather encompasses all variations which are evident as a result of the teaching provided herein.

Example 1

1 kilogram of the aerial part comprising mainly the leaves and stems of the plant *Centella asiatica*, are taken in a clean and dry form, and pulverized to a size ensuring 100% pass through in a 20 mesh sizes hammer mill. This material was extracted with 5 liters of isopropyl alcohol in a fixed bed counter current extractor repeatedly over a period of 8 hrs at 30° C. After 8 hrs the extract was filtered clean of all suspended matters. The clear filtrate was concentrated to a semisolid at 40 in a rotary evaporator under vacuum. To the concentrated mass 3 liters of deionised water is added to get a Homogenous liquid. The liquid was extracted by washing it twice with 2 liters of hexane and the bottom aqueous layer was separated out. The aqueous layer was again extracted twice with 1 liter of methylisobutylketone. The bottom aqueous layer was separated and passed through an adsorbent resin Amberlite XAD1180 (400 ml) bed maintaining a flow rate of 25 ml per minute and the out flow was monitored for the absence of terpenoid glycosides.

The column was washed thoroughly with 5 liters of Demineralised water until the washings are colorless. The adsorbents column was eluted with ethyl alcohol until the monitoring TLC test showed absence of terpenoid glycosides. The resultant elute was passed through a column comprising of 100 grams of activated charcoal and 250 grams of silica gel of the size 60 to 120 mesh. The resultants elute collected and the column washed thoroughly with ethyl alcohol and all the washings combined with elute and concentrated in a vacuum distillation facility at 45 to 50 to get powder. This powder was dissolved in 300 ml Demineralised water to get clear solution of solid content of 20% and spray dried in a co-current indirect hot air spray dryer under following conditions.

Inlet temperature: 140° C.
Outlet temperature: 80° C.

The yield of 30 gm of pale yellow, water soluble powder with a composition of 40% asiaticoside, and 36% madecassoside was obtained by the HPLC method.

Example 2

1 kilogram of the aerial part comprising mainly the leaves and stems of the plant *Centella asiatica*, are taken in a clean and dry form, and pulverized to a size ensuring 100% pass through in a 20 mesh sizes hammer mill. This material was extracted with 5 liters of ethyl alcohol in fixed bed counter current extractor repeatedly over a period of 8 hrs at 30° C. After 8 hrs the extract was filtered clean of all suspended matters. The clear filtrate was concentrated to a semisolid at 40° C. in a rotary evaporator under vacuum. To the concentrated mass 3 liters of deionised water is added to get a Homogenous liquid. The liquid was extracted by washing it twice with 2 liters of hexane and the bottom aqueous layer was separated out. The aqueous layer was again extracted twice with 1 liter of methyl isobutyl ketone. The bottom aqueous layer was separated and passed through a bed of adsorbent resin Amberlite XAD1180 (400 ml) bed maintaining a flow rate of 25 ml per minute ant the out flow was monitored for the absence of *centello saponins*.

The column was washed thoroughly with 5 liters of Demineralised water until the washings are colorless. The adsorbents column was eluted with ethyl alcohol until the monitoring TLC test showed absence of *centello saponins*. The resultant elute was passed through a column comprising of 100 grams of activated charcoal and 250 grams of silica gel of the size 60 to 120 mesh. The resultant elute was collected and the column washed thoroughly with isopropyl alcohol and all the washings combined with elute and concentrated in a vacuum distillation facility at 45° C. to 50° C. to get powder. This powder was dissolved in 300 ml of Demineralised water to get clear solution of solid content of 10% and spray dried in a co-current indirect hot air spray dryer under following conditions.

Inlet temperature: 140° C.
Outlet temperature: 80° C.

The yield of 28 gm of pale yellow, water soluble powder with a composition of 40% asiaticoside, and 34% madecassoside was obtained by the HPLC method.

Example 3

1 kilogram of the aerial part comprising mainly the leaves and stems of the plant *Centella asiatica*, are taken in a clean and dry form, and pulverized to a size ensuring 100% pass through in a 20 mesh sizes hammer mill. This material was extracted with 5 liters of methyl alcohol in fixed bed counter current extractor repeatedly over a period of 8 hrs at 30° C. after 8 hrs the extract was filtered clean of all suspended matters. The clear filtrate was concentrated to a semisolid at 40 in a rotary evaporator under vacuum. To the concentrated mass 3 liters of deionised water is added to get a homogenous liquid. The liquid was extracted by washing it twice with 2 liters of hexane and the bottom aqueous layer was separated out. The aqueous layer was again extracted twice with 1 liter of methyl isobutyl ketone. The bottom aqueous layer was separated and passed through a bed of adsorbent resin Amberlite XAD1180 (400 ml) bed maintaining a flow rate of 25 ml per minute ant the out flow was monitored for the absence of *centello saponins*.

The column was washed thoroughly with 5 liters in excess of Demineralised water until the washings are colorless. The adsorbents column was eluted with isopropyl alcohol until the monitoring TLC test showed an absence of *centello saponins* in the elute. The resultant elute was passed through a column comprising of 100 grams of activated charcoal and 250 grams of silica gel of the size 60 to 120 mesh. The resultant elutes collected and the column washed thoroughly with isopropyl alcohol and all the washings combined with elute and concentrated in a vacuum distillation facility at 45 to 50 to get powder. This powder was dissolved in 300 ml Demineralised water to get clear solution of solid content of 20% and spray dried in a co-current indirect hot air spray dryer under following conditions.

Inlet temperature: 140° C.
Outlet temperature: 80° C.

The yield of 32 gm of pale yellow, water soluble powder with a composition of 39% asiaticoside, and 34% madecassoside was obtained by the HPLC method.

Example 4

1 kilogram of the aerial part comprising mainly the leaves and stems of the plant *Centella asiatica*, are taken in a clean and dry form, and pulverized to a size ensuring 100% pass through in a 20 mesh sizes hammer mill. This material was extracted with 5 liters of methyl alcohol in fixed bed counter current extractor repeatedly over a period of 10 hrs at 30° C. after 10 hrs the extract was filtered clean of all suspended matters. The clear filtrate was concentrated to a semisolid at 40 in a rotary evaporator under vacuum. To the concentrated mass 3 liters of deionised water is added to get a Homogenous liquid. The liquid was extracted by washing it twice with 2 liters of hexane and the bottom aqueous layer was separated out. The aqueous layer was again extracted twice with 1 liter of methyl isobutyl ketone. The bottom aqueous layer was separated and passed through a bed of adsorbent resin Amberlite XAD1180 (400 ml) bed maintaining a flow rate of 25 ml per minute ant the out flow was monitored for the absence of *centello saponins*.

The column was washed thoroughly with 5 liters in excess of Demineralised water until the washings are colorless. The adsorbents column was eluted free with ethyl alcohol until the monitoring TLC test showed absence of *centello saponins* in the elute. The resultant elute was passed through a column comprising of 100 grams of activated charcoal and 250 grams of silica gel of the size 60 to 120 mesh. The resultant elutes were collected and the column was washed thoroughly with ethyl alcohol and all the washings combined with elute and concentrated in a vacuum distillation facility at 45-50 to get powder. This powder was dissolved in 300 ml Demineralised water to get clear solution of solid content of 20% and spray dried in a co-current indirect hot air spray dryer under following conditions.

Inlet temperature: 140° C.
Outlet temperature: 80° C.

The yield of 30 gm of pale yellow, water soluble powder with a composition of 41% asiaticoside, and 36% madecassoside was obtained by the HPLC method.

Example 5

Effect of Test Compound on Tail Suspension in Mice

This test is used to evaluate potential antidepressants by determining the percentage decrease in immobility in rodents. The immobility displayed by rodents in captivity when subjected to an unavoidable stress is hypothesized to reflect a behavioral despair, which may reflect the state of mind of a human being suffering from the depressive disorder. Clinically effective anti-dependents reduce the immobility that mice display after active and unsuccessful attempts to escape when suspended by tail.

Procedure:

Swiss albino mice of either sex weighing 25-30 g would be housed in plastic cages for at least 10 days prior to testing. Animals would be allowed to adapt to the testing environment for 1 hr before testing. Groups of 6 animals would be treated orally with the test drug, the vehicle or the standard drug 60 minutes prior to testing. For the test, the mice would be suspended on the edge of a shelf 58 cm above a tabletop by adhesive tape placed approximately 1 cm from the tip of the tail. The duration of immobility would be recorded for a period of 6 min continuously. Mice are considered immobile when they hang passively and completely motionless for at least 1 min. Imipramine 64 mg/kg, p.o. would be used as standard.

The percentage of animals showing the passive behavior is counted and compared with vehicle treated controls using various doses.

Effect of Test Drug on immobility time

| TREATMENT | TOTAL IMMOBILITY TIME(SEC) | % DECREASE IN IMMOBILITY |
|---|---|---|
| Vehicle | 188.91 ± 7.412 | — |
| Test Drug(3 mg/kg) | 163.27 ± 12.240 | 13.57 |
| Test Drug(10 mg/kg) | 132.10 ± 8.201** | 30.08 |
| Test Drug(30 mg/kg) | 112.69 ± 10.620** | 40.34 |
| Imipramine(64 mg/kg) | 90.90 ± 7.690** | 51.88 |

Data represent mean ± SEM (n = 8)
**P < 0.01 vs vehicle, data analyzed by ANOVA followed by Dunnett's test The result obtained in this test showed a dose dependent decrease in the immobility by the test drug at 3, 10 and 30 mg/kg dose, p.o. At 10 and 30 mg/kg dose the decrease in immobility was significant ($P<0.01$). The percent decrease in immobility was calculated against the vehicle group. The standard drug, imipramine (64 mg/kg, p.o.) showed significant (P<0.01) decrease in immobility.

Example 6

Effect of Test Compound on Locomotor Activity in Mice

This test is conducted to rule out the sedative aspect of the anti-depressants. Besides, it can also eliminate certain muscle relaxant effects of the drug. Swiss albino mice are tested in a locomotors chamber with laser sensors to check their movements. The locomotors score is a direct function of the mobility of the animal. Decrease in mobility could be due to sedative effect and muscle relaxant effect.

Procedure:

Swiss albino mice of either sex weighing 25-30 g would be housed in plastic cages for at least 10 days prior to testing. Animals would be allowed to adapt to the testing environment for 1 hr before testing. Groups of 6 animals would be treated with the test drug (10, 30 & 100 mg/kg, p.o.) or the vehicle or standard drug orally 60 min prior to testing. For the test the mice would be individually placed in Actophotometer. Locomotor activity would be counted for 10 minutes duration individually. Imipramine 64 mg/kg, p.o. would be used as standard.

| Effect of Test Drug on immobility time | | |
|---|---|---|
| TREATMENT | TOTAL LOCOMOTOR ACTIVITY COUNTS | % INCREASE IN LOCOMOTOR ACTIVITY |
| Vehicle | 207.50 ± 21.88 | — |
| Test Drug(3 mg/kg) | 220.75 ± 11.25 | 6.39 |
| Test Drug(10 mg/kg) | 233.13 ± 15.80 | 12.35 |
| Test Drug(30 mg/kg) | 289.38 ± 15.51** | 39.46 |
| Imipramine(64 mg/kg) | 127.00 ± 06.90** | −38.80 |

Data represent mean ± SEM (n = 8)
**P < 0.01 vs vehicle, data analyzed by ANOVA followed by Dunnett's test Imipramine is a positive control and brings about reduction in locomotors activity. This is an indication of sedation effect of the drug. Whereas the test drug is showing dose dependant increase in locomotors activity, thus confirming that there is no sedation effect. It is pertinent to note that Imipramine induces sedation. Therefore the test compound does not have the side effect of sedation as seen in tricyclic anti depressant drug.

The test drug, at 30 mg/kg, p.o showed significant (P<0.01) increase in locomotor activity. At 3 and 10 mg/kg dose the increase in locomotor activity however was not significant. The percent increase in locomotor activity was calculated against the vehicle group. The standard drug, imipramine (64 mg/kg, p.o.) showed significant (P<0.01) increase in locomotor activity, but, which was less than vehicle and test drug.

Example 7

Forced Swim Test

Mice forced to swim in a restricted space from which they cannot escape are induced to a characteristic behavior of immobility.

Procedure:

Male Swiss albino mice weighing 25-30 g would be brought into the laboratory at least one day before the experiment and would be housed separately in cages. Mice would be individually forced to swim inside a vertical Plexiglas cylinder (25×23 cm) containing 12 cm of water maintained at 25° C. Mice, placed in the cylinders for the first time are initially highly active, vigorously swimming in circles, trying to climb the wall or diving to the bottom. After 2-3 min activity begins to subside and to be interspersed with phases of immobility or floating of increasing length. After 5-6 min immobility reaches a plateau where the mice remain immobile for approximately 80% of the time. After 15 min in the water the mice would be removed and would be allowed to dry in a heated enclosure (32° C.) before being returned to their home cages. They would again be placed in the cylinder 24 hr later and the total duration of immobility would be counted for the last 4 min of 6 min test session. An animal is judged to be immobile whenever it remains floating passively in the water in a slightly hunched but upright position, its nose just above the surface. Test drug (10, 30 & 100 mg/kg, p.o.) or vehicle or standard drug, Imipramine (100 mg/kg, p.o.) would be administered one hour prior to testing.

| Effect of Test Drug on immobility time | | |
|---|---|---|
| TREATMENT | TOTAL IMMOBILITY TIME(SEC) | % DECREASE IN IMMOBILITY |
| Vehicle | 158.17 ± 8.991 | — |
| Test Drug(3 mg/kg) | 142.50 ± 3.847 | 9.90 |
| Test Drug(10 mg/kg) | 86.32 ± 15.920** | 45.42 |
| Test Drug(30 mg/kg) | 49.43 ± 3.584** | 68.75 |
| Imipramine(100 mg/kg) | 45.17 ± 4.450** | 71.44 |

Data represent mean ± SEM (n = 6)
**P < 0.01 vs vehicle, data analyzed by ANOVA followed by Dunnett's test The result obtained in this test showed that Test Drug produced dose dependent decrease in the immobility at 3, 10 and 30 mg/kg, p.o. At 10 and 30 mg/kg dose the decrease in immobility were significant (P<0.01). Percent decrease in immobility was calculated against the vehicle group. Readings of individual animal are shown in appendix II, page-113. The decrease in immobility showed by 30 mg/kg dose Reserpine Antagonism Depletion of biogenic amines in brain induces not only catalepsy but also hypothermia in rodents. The decrease of body temperature induced by reserpine is antagonized by antidepressants, MAO-inhibitors and central stimulants. Reserpine also decreases the levels of brain neuroamines like serotonin. Hence an anti-depressant should be capable of reversing the effects of Reserpine.

Example 8

Forced Swim Test after Reserpine Administration

Procedure:

Male Swiss albino mice weighing 25-30 g would be used. All the animals would be Pre trained individually to swim for 15 minutes in vertical plexiglass cylinder (25×23 cm) containing 12 cm of water maintained at 25° C. They would be injected with 5 mg/kg reserpine i.p. after 20 hr of pretraining. Four hours after reserpine administration, test drug (10, 30 & 100 mg/kg) or vehicle or standard drug would be administered orally. Then after 60 min of treatment the animals would be individually forced to swim for 6 min during which the immobility would be recorded. Imipramine 64 mg/kg, p.o. would be used as standard.

| Effect of Test Drug on immobility time after Reserpine administration | | |
|---|---|---|
| TREATMENT | TOTAL IMMOBILITY TIME(SEC) | % DECREASE IN IMMOBILITY |
| Vehicle | 146.29 ± 12.07 | — |
| Reserpine (5 mg/kg) | 221.60 ± 6.793# | — |
| Test Drug(10 mg/kg) | 185.72 ± 10.30 | 15.99 |
| Test Drug(30 mg/kg) | 139.92 ± 13.54** | 36.71 |
| Test Drug (100 mg/kg) | 096.72 ± 7.529** | 56.25 |
| Imipramine(100 mg/kg) | 063.57 ± 3.320** | 71.24 |

Data represent mean ± SEM (n = 6)
P < 0.05 vs vehicle,
**P < 0.01 vs reserpine, data analyzed by ANOVA followed by Dunnett's test The result obtained in this test showed dose dependent decrease in the immobility at 10, 30 and 100 mg/kg dose, p.o. of test drug. However, 30 and 100 mg/kg dose showed significant (P<0.01) decrease in immobility as compared to reserpine group. The percent decrease in immobility was calculated against reserpine group. The standard drug, imipramine (64 mg/kg) also showed a significant (P<0.01) decrease in the immobility.

Example 9

Locomotor Activity Test after Reserpine Administration

Depletion of biogenic amines in brain induces not only catalepsy, ptosis, hypothermia but also reduced locomotor activity in rodents. The intra-peritoneal administration of reserpine (5 mg/kg, i.p.) in mice leads to reduce locomotor activity which can be antagonized by antidepressants, MAO-inhibitors and central stimulants.

Procedure:

Male Swiss albino mice weighing 25-30 g would be used. They would be administered with 5 mg/kg Reserpine i.p. Four hours after Reserpine administration, test drug (10, 30 & 100 mg/kg) or vehicle or standard drug would be administered orally. Then after 60 min of treatment the animals would be individually placed in acto-photometer for 10 min during which the locomotor activity would be counted. Imipramine 64 mg/kg, p.o. would be used as standard.

| Effect of Test Drug on locomotor activity after Reserpine administration | | |
|---|---|---|
| TREATMENT | TOTAL LOCOMOTOR ACTIVITY COUNTS | % INCREASE IN LOCOMOTOR ACTIVITY |
| Vehicle | 280.5 ± 31.79 | — |
| Reserpine(5 mg/kg) | 121.17 ± 06.112## | — |
| Test Drug(10 mg/kg) | 242.33 ± 04.372* | 100.00 |
| Test Drug(30 mg/kg) | 282.17 ± 08.662*** | 132.87 |
| Test Drug(100 mg/kg) | 214.33 ± 18.33 | 076.88 |
| Imipramine(64 mg/kg) | 218.00 ± 21.48 | 079.91 |

Data represent mean ± SEM (n = 6)
P < 0.01 vs vehicle,
*P < 0.05 vs reserpine,
***P < 0.001 vs reserpine, data analyzed by Kruskal-Wallis test followed by Dunn's test.

The result obtained in this test showed dose independent effect of increase in the locomotor activity at the dose of 10, 30 and 100 mg/kg, p.o. of test drug. However, at dose 10 mg/kg (P<0.05) and 30 mg/kg (P<0.001) dose of test drug showed significant activity as compared to reserpine group. The percent increases in locomotor activity were calculated against reserpine group. The standard drug, imipramine (64 mg/kg) did not show significant increase in the locomotor activity.

Example 10

5-Hydroxytryptophan (L 5-HTP) Potentiation in Mice

Several antidepressant agents potentiate serotonin effects by a block of the re uptake of serotonin. 5-Hydroxytryptophan is used as the precursor of serotonin.

Procedure:

Groups of 6 Swiss albino mice (25-30 g) would be used. They would be treated with the test drug (10, 30 & 100 mg/kg, p.o.) or the vehicle or standard drug 60 min before 75 mg/kg i.p. L-5-hydroxytryptophan (5-HTP). The mice would be then placed into glass bell jars and the number of head twitches would be counted in five 2-min intervals (between 14 and 16, 24 and 26, 34 and 36, 44 and 46 and 54 and 56 min). Fluoxetine 100 mg/kg, p.o. and imipramine 64 mg/kg, p.o. would be used as standard.

| Effect of Test Drug on head twitches in 5-HTP potentiation | | |
|---|---|---|
| TREATMENT | TOTAL NO OF HEAD TWITCHES MEAN ± SEM | % INCREASE IN NO OF HEAD TWITCHES |
| Vehicle | 21.625 ± 1.752 | — |
| Test Drug(10 mg/kg) | 52.625 ± 6.050 | 143.35 |
| Test Drug(30 mg/kg) | 62.250 ± 6.239 | 187.86 |
| Test Drug(100 mg/kg) | 95.375 ± 4.617*** | 341.04 |
| Fluoxetine(100 mg/kg) | 108.750 ± 3.702*** | 402.89 |
| Imipramine(64 mg/kg) | 13.25 ± 2.477 | −38.73 |

Data represent mean ± SEM (n = 8)
***P < 0.001 vs vehicle, data analyzed by Kruskal-Wallis followed by Dunn's multiple comparison test The result obtained in this test showed significant (P<0.001) increase in the head twitches at the dose 100 mg/kg, p.o. of test drug. The effect was dose dependent. The percent increase in head twitches were calculated against the vehicle group. The standard drug, fluoxetine (100 mg/kg, p.o.) showed significant (P<0.001) increase in the head twitches, but, imipramine (64 mg/kg, p.o.) did not show significant increase in the head twitches.

It is observed that animals administered Fluoxetine had diarrhea and exhibited agitation. Whereas test drug group of animals did not have any diarrhea and these animals were not agitated. The test drug is equally powerful as Fluoxetine without the usual side effects.

Example 11

Effect of Test Drug on Structure of Gastric Mucosa

6 Wistar rats were treated with the test drug. The test drug was dosed at 3 doses, namely: 30, 6, and 120 mg/kg orally. Six hours after administration, the animals were sacrificed by cervical dislocation and the stomach was dissected out. It was cut along the greater curvature and washed with saline.

FIG. 1 represents the stomach of the animal treated with a test drug dose of 30 mg/kg.

Figure 2:
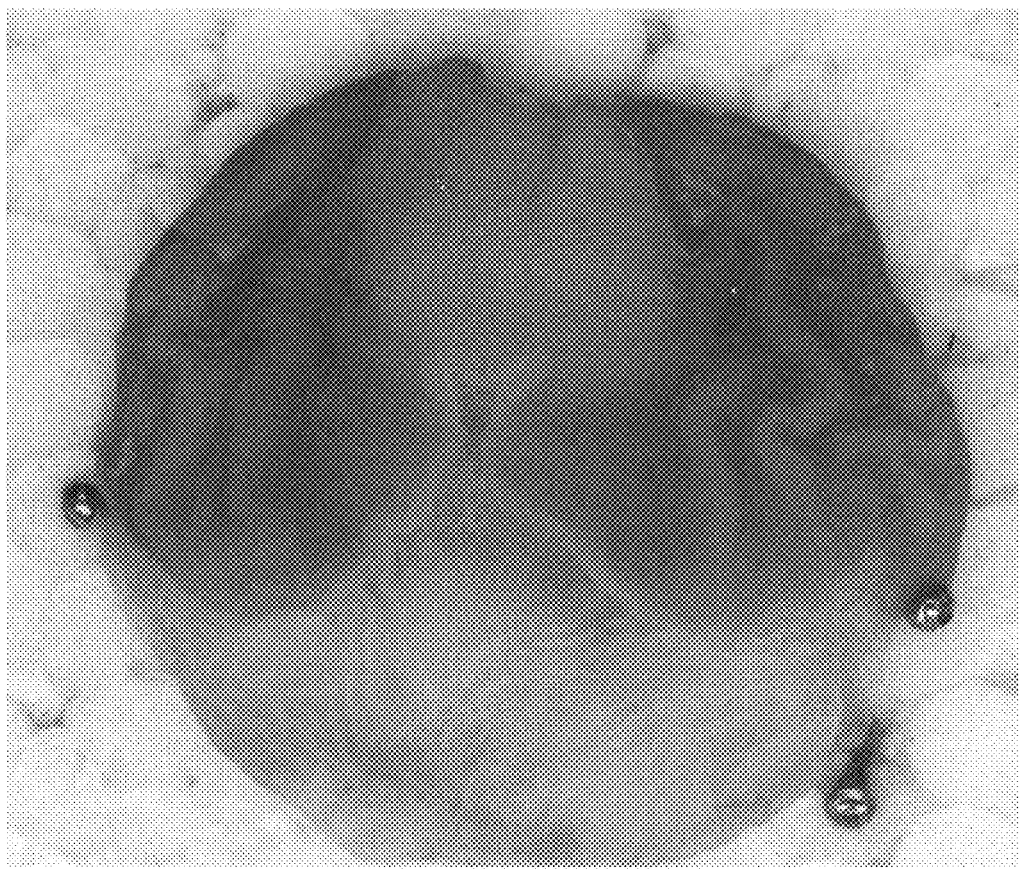
FIG. 2 is an image that represents the stomach of the animal treated with a test drug dose of 60 mg/kg.

FIG. 2 represents the stomach of the animal treated with a test drug dose of 60 mg/kg.

Figure 3:
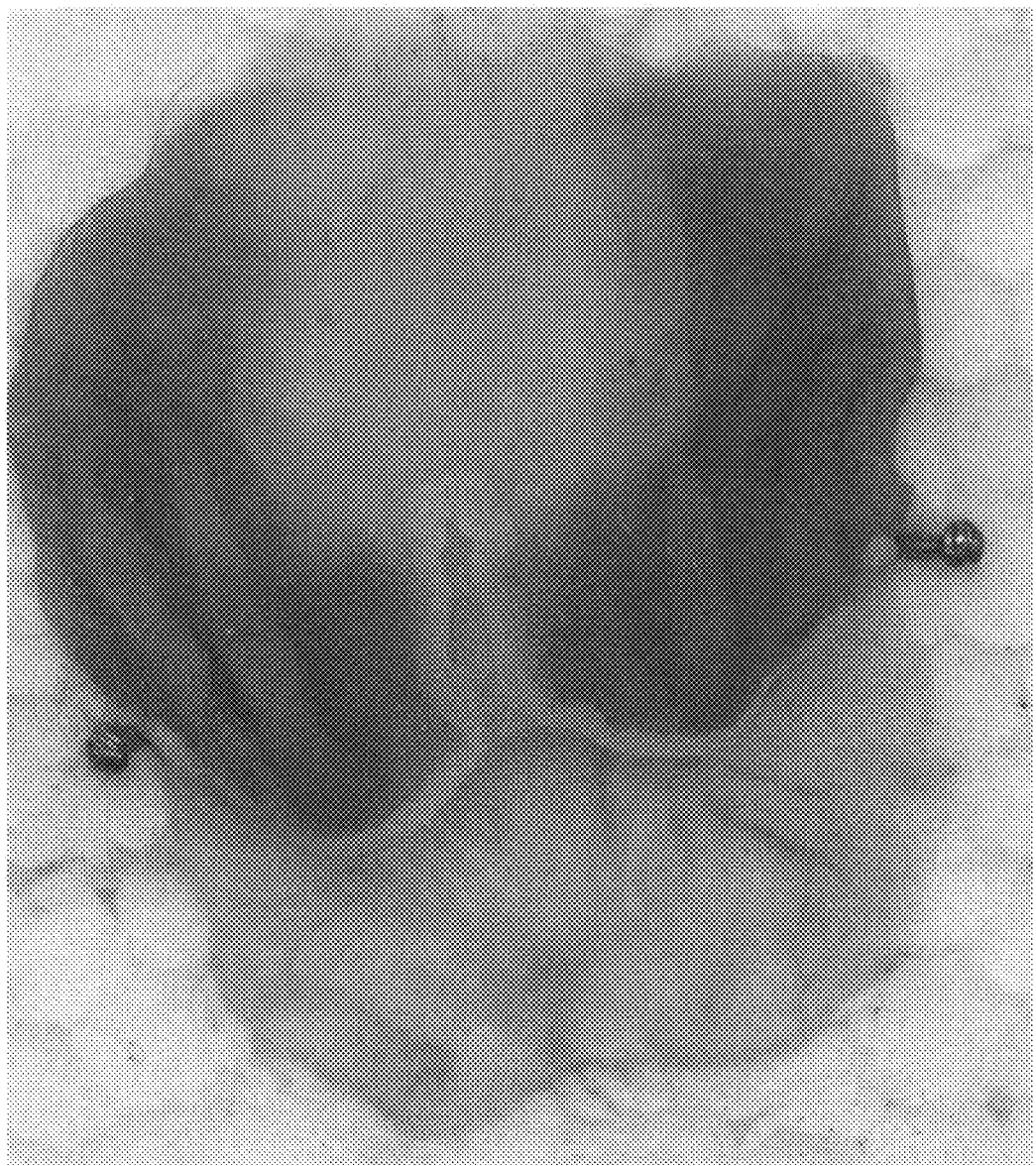
FIG. 3 is an image that represents the stomach of the animal treated with a test drug dose of 120 mg/kg.

FIG. 3 represents the stomach of the animal treated with a test drug dose of 120 mg/kg.

These figures show "ridges" in the glandular part of the stomach. The ridges increase in a dose dependant fashion with the test drug. Test Drug doses of 60 mg/kg and 120 mg/kg show more prominent ridge formation. These ridges indicate the contractility of the stomach. Hence increase in ridge formation implies an increased peristaltic movent in the stomach. This movement is indicative of a higher rate of gastric emptying.

The above description is illustrative of the various embodiments of the invention and is not to be construed as limiting, it being understood that a person skilled in the art may carry out many obvious variations to the present invention.

The disclosure of every patent, patent application, and publication cited herein is hereby incorporated herein by reference in its entirety.

What is claimed is:

1. A pharmaceutical composition for treating serotonin mediated disorders, the composition consisting of asiaticoside at a concentration ranging from 15-50 wt/wt % and madecassoside at a concentration ranging from 20-36 wt/wt %, optionally along with pharmaceutically acceptable excipients.

2. The composition as claimed in claim 1, wherein the excipients are present and are selected from the group consisting of granulating agents, binding agents, lubricating agents, disintegrating agents, sweetening agents, glidants, anti-adherents, anti-static agents, surfactants, anti-oxidants, gums, coating agents, coloring agents, flavoring agents, plasticizers, preservatives, suspending agents, emulsifying agents and spheronization agents.

3. The composition as claimed in claim 1, wherein the composition is formulated into various dosage forms selected from the group consisting of tablets, troches, lozenges, aqueous or oily suspensions, ointments, patches, gels, lotions, dentifrices, capsules, emulsions, creams, sprays, drops, dispersible powders or granules, emulsion in hard or soft gel capsules, syrups, elixirs, phytoceuticals, nutraceuticals and food stuffs.

4. The composition as claimed in claim 1, wherein the composition, when administered to a subject, inhibits the reuptake of serotonin.

5. The composition as claimed in claim 1, wherein the composition when administered to a subject, has a therapeutic effect on serotonin mediated disorders selected from the group consisting of depression, obesity, gastric emptying, and mood elevation by inhibiting the reuptake of serotonin.

6. A process for preparing the composition of claim 1, wherein said process comprises the steps of:
   a. filtering and concentrating an extract obtained from plant *Centella asiatica*;
   b. dissolving the concentrated extract in a solvent to obtain a solution;
   c. treating the solution with the solvents to remove fatty substances, chlorophyll and other colorants;
   d. passing the treated solution through adsorbents in a column and washing it with a solvent to obtain an elute; and
   e. concentrating the clear solution to obtain the composition.

7. The process of claim 6, wherein the solvent is selected from the group consisting of heterocyclic aromatic compounds, aliphatic compounds, ketones, alcohols, nitrites, esters, ether and mixtures of one or more thereof.

8. The process of claim 6, wherein the solvent used for extraction is preferably an aliphatic alcohol.

9. The process of claim 6, wherein the extraction is carried out at temperature ranging from 20° C. to 38° C.

10. The process of claim 9, wherein the extraction is carried out at a temperature of 30° C.

11. The process of claim 6, wherein the extraction is carried out for 6 h to 10 h.

12. The process of claim 11, wherein the extraction is carried out for 8 h.

13. The process of claim 6, wherein the concentration is carried out at a temperature ranging from 40° C. to 50° C.

14. The process of claim 13, wherein the concentration is carried out at 45° C.

15. The process of claim 6, wherein the concentrated extract is dissolved in a solvent comprising deionized water.

16. The process of claim 6, wherein the solvent in which the fatty substances are removed is selected from a group comprising hexane, petroleum ether and methylisobutylketone.

17. The process of claim 6, wherein the adsorbent is selected from the group consisting of resin, charcoal, silica gel and mixtures thereof.

18. The process of claim 6, wherein the final elute is concentrated at temperature ranging from 50° C. to 65° C.

19. A method for managing serotonin-mediated disorders in a patient in need thereof, comprising administering a composition consisting of asiaticoside at a concentration ranging from 15-50 wt/wt % and madecassoside at a concentration ranging from 20-36 wt/wt % optionally along with pharmaceutically acceptable excipients.

20. The method of claim 19, wherein the patient is a human.

21. The method of claim 19, wherein the composition is administered at a dosage ranging from 1-15 mg/kg body weight in a human patient.

22. The method of claim 19, wherein the serotonin-mediated disorders are depression, obesity, gastric emptying, or mood elevation.

23. The method of claim 19, wherein the composition is non-toxic and free of adverse effects.

* * * * *